United States Patent
Sakazume et al.

[11] Patent Number: 5,985,215
[45] Date of Patent: Nov. 16, 1999

[54] ANALYZING APPARATUS HAVING A FUNCTION PIPETTE SAMPLES

[75] Inventors: Taku Sakazume, Hitachinaka; Hiroshi Mitsumaki, Mito; Tomonori Mimura, Tomobe-machi; Kazumitsu Kawase, Hitachinaka, all of Japan

[73] Assignee: Hitachi, Ltd., Tokyo, Japan

[21] Appl. No.: 08/934,664

[22] Filed: Sep. 22, 1997

[30] Foreign Application Priority Data

Sep. 24, 1996 [JP] Japan ..................... 8251469

[51] Int. Cl.⁶ .................................. G01N 35/10
[52] U.S. Cl. .................. 422/67; 422/63; 422/65; 422/81; 422/100; 422/105; 422/108; 436/43; 436/47; 436/48; 436/49; 436/50; 436/54; 73/864.23; 73/864.24
[58] Field of Search ................... 422/63, 65, 67, 422/68.1, 100, 81, 104, 105, 108; 436/43, 47, 48, 50, 49, 54; 73/864.21, 864.23, 864.24

[56] References Cited

U.S. PATENT DOCUMENTS

| | | |
|---|---|---|
| 4,259,571 | 3/1981 | Dubberly . |
| 4,751,186 | 6/1988 | Baisch et al. ................ 436/47 |
| 4,885,461 | 12/1989 | Mattila et al. . |
| 5,013,529 | 5/1991 | Itoh ........................... 422/100 |
| 5,201,232 | 4/1993 | Uffenheimer ............. 73/864.23 |
| 5,207,986 | 5/1993 | Kadota et al. . |
| 5,221,519 | 6/1993 | Wuerschum ................ 422/65 |
| 5,378,433 | 1/1995 | Duckett et al. ............ 422/100 |
| 5,391,499 | 2/1995 | Karkantis et al. . |
| 5,420,408 | 5/1995 | Weyrauch et al. ......... 235/454 |
| 5,424,036 | 6/1995 | Ushikubo ..................... 422/64 |
| 5,517,867 | 5/1996 | Ely et al. . |
| 5,663,545 | 9/1997 | Marquiss .................... 235/375 |
| 5,700,429 | 12/1997 | Buhler et al. .............. 422/104 |
| 5,777,303 | 7/1998 | Berney ....................... 235/375 |

FOREIGN PATENT DOCUMENTS

| | | |
|---|---|---|
| 692 717 | 1/1996 | European Pat. Off. . |
| 40 23 149 | 1/1992 | Germany . |
| 40 23 165 | 1/1992 | Germany . |
| 43 14 180 | 11/1993 | Germany . |
| 6-27745 | 4/1994 | Japan . |
| WO90/08307 | 7/1990 | WIPO . |

Primary Examiner—Long V. Le
Attorney, Agent, or Firm—Fay, Sharpe, Beall, Fagan, Minnich & MCKee

[57] ABSTRACT

In an analyzing apparatus of the present invention, sample racks, in each of which a plurality of sample containers are held, are transferred from a rack feeding unit to a discrimination unit for discriminating a type of each sample container. After the discrimination unit, a plurality of analyzing units are installed along a transfer line, and pipetters of different types are provided in the respective analyzing units. The discrimination unit detects information on the length and the width of each sample container held in each sample rack by using an optical detector. A control part selects one of the analyzing units, suitable for analyzing the sample container of which type was discriminated, based on the information detected by the discrimination unit, and transfers the sample container of which type was discriminated, to a sample pipetting position in the selected analyzing unit.

11 Claims, 4 Drawing Sheets

ANALYZING APPARATUS HAVING A FUNCTION PIPETTE SAMPLES

BACKGROUND OF THE INVENTION

1. Field of the Invention

The present invention relates to an automatic analyzing apparatus having a function to pipette samples, and especially to an analyzing apparatus suitable for dealing with various and many sample containers.

2. Description of Related Art

In an analyzing system for pipetting biological samples such as blood, urine, etc., contained in sample containers, and analyzing substances included in the samples, a remarkable tendency to decrease an amount of a pipetted sample to a very small quantity has been seen, mainly in order to reduce the pain of a patient from which samples are collected, and the consumption amount of reagent. Moreover, the scope of items to be analyzed has been enlarged, and highly increasing the sensitivity to analyze biological components of a very low concentration has been also required. Consequently, various types of sample pipetting devices which can more correctly pipette a very small quantity of sample (less than microliters) to reduce contamination between samples, have been recently adopted.

Furthermore, in a conventional analyzing apparatus as that disclosed in U.S. Pat. No. 5,207,986 ( JP-A-27745/1994), the same two analyzing units are serially arranged along a sample container conveying line, and a sample is pipetted from a sample container by a pipetter provided at each analyzing unit. The pipetted sample is discharged into a reaction container, and analyzed by each analyzing unit.

Generally, inabiological inspection, different kinds of samples such as blood serum, urine, etc., have been collected, specified, and analyzed by using different analyzing apparatuses. Therefore, a plurality of analyzing apparatuses have been needed, corresponding to different kinds of biological samples.

In collecting different kinds of samples, or samples in different diagnosis sections in hospitals, various types of sample containers are usually used. Furthermore, various kinds of sample pipetting devices are used, corresponding to the processing ability of each analyzing apparatus, and also to kinds of analyzing methods such as a method using chemical reactions, a method using immnunological reactions and so forth.

SUMMARY OF THE INVENTION

Objective of the Invention:

An objective of the present invention is to provide an analyzing apparatus which can continuously perform pipetting processes of samples collected in many and various types of sample containers.

Method of Solving the Problems:

A feature of an analyzing apparatus in the present invention is in that the analyzing apparatus comprises:

discrimination means for discriminating a type of a sample container placed at a discrimination position;

plural types of sample pipetting means having different sizes and/or numbers of pipette nozzles;

transfer means for transferring the sample container of which type is discriminated by the discrimination means; and control means for controlling the transfer means so that after a type of the sample container has been discriminated, the sample container is transferred to a position of one of the sample pipetting means, the one being suitable for pipetting the sample contained in the container of which type was discriminated.

Another feature of an analyzing apparatus in the present invention is in that the analyzing apparatus comprises:

discrimination means for discriminating a type of a sample container placed at a discrimination position;

nozzle tip feeding means for allocating and connecting an exchangeable pipette nozzle tip suitable for pipetting the sample contained in the container of which type was discriminated, to a nozzle part of a pipetting device; and pipette means for pipetting the sample contained in the container of which type was discriminated, after the allocated nozzle tip was connected to the sample container.

DETAILED DESCRIPTION OF THE EMBODIMENTS

Details of the first feature of the present invention will be explained with an embodiment shown in FIG. 1–FIG. 5.

Figure 1:
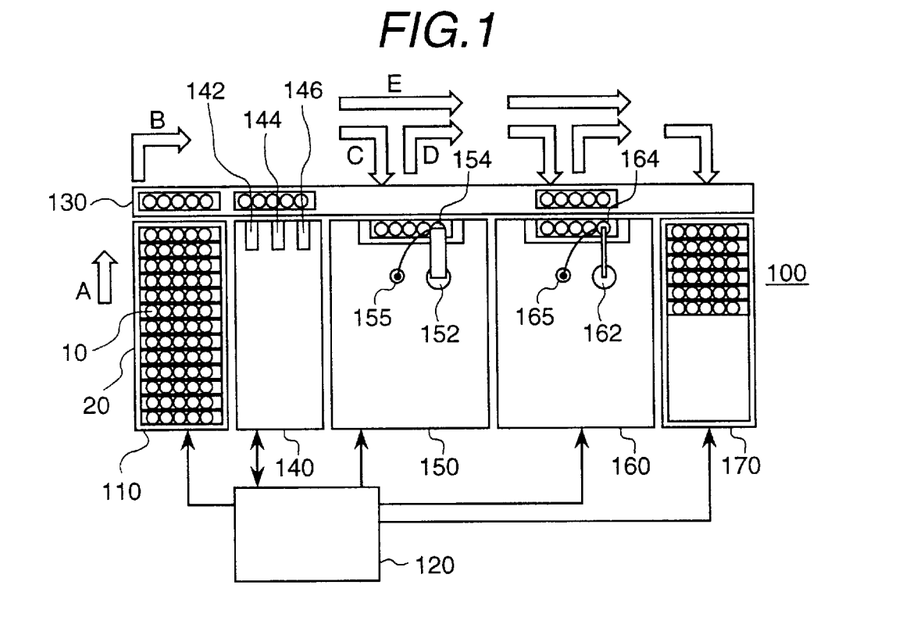
FIG. 1 shows a composition of an analyzing apparatus in an embodiment of the present invention.

In FIG. 1, an analyzing apparatus 100 comprises a rack feeding unit 110, a transfer line 130, a discrimination unit 140, the first analyzing unit 150, the second analyzing unit 160, a rack collecting unit 170, and a control part 120 for controlling the above units or components.

Figure 3:
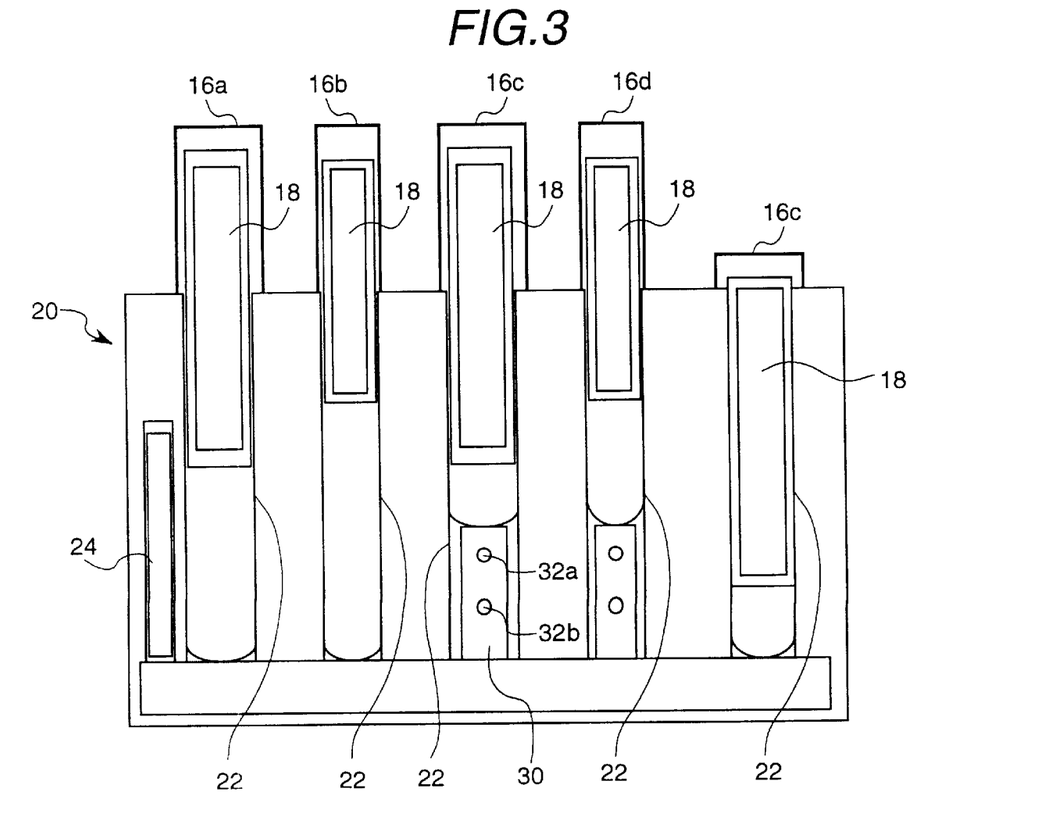
FIG. 3 is a front view of an example of a sample rack loading various types of sample containers to which bar code labels are affixed.

Sample racks 20 which are loaded with a plurality of sample containers 10, each of which contains a liquid sample, are set in the rack feeding unit 110. The sample rack 20 is a rectangular parallelepiped holder, and it has plural holding holes into which sample containers are inserted. In the illustrated example, the sample rack 20 can hold five sample containers 10. As shown in FIG. 3, slots or windows 22 are formed at one or both sides of the sample rack 20, corresponding to the respective holes into which the respective sample containers 10 are inserted, so that the respective inserted containers can be viewed from the outside of the rack 20.

When an operator gives a command for starting a sample analyzing process to the control part 120, the control part 120 controls the transfer line 130 so as to transfer the sample rack 20 to the position of the discrimination unit 140. That is, a plurality of sample racks in the rack feeding unit 110 are transferred in order in the direction shown with an arrow mark A, and laid on the transfer line 130. Each sample rack 20 laid on the transfer line 130 is conveyed to the position of the discrimination unit 140 by moving the transfer line 130. The moving direction of the sample racks 20 is shown with an arrow mark B. The transfer line 130 includes a belt conveyer driven by a pulse motor not shown in the figure.

The discrimination unit 140 includes a bar code reader 142 for reading a rack bar code label 24 affixed to each sample rack 20 to show information on the sample rack, a bar code reader 144 for reading a sample container bar code label 18 affixed to each sample container 10 to show information on a sample in the container 10, etc., and a container type discrimination part 146 for reading size information on the length and the width (diameter) of each sample container. The type or shape of each sample container is determined by the discrimination unit 140 and the control part 120. The positions to which the rack bar code label and the sample container bar code label are affixed, are shown in FIG. 3.

After a type or a size of each sample container 10 in the sample rack 20 has been discriminated, the rack 20 is conveyed to the position of the first analyzing unit 150 or the second analyzing unit 160, by the transfer line 130. Each of the first and second analyzing units 150 and 160 includes a movable reaction disk on which a plurality of reaction cuvettes (containers) are arranged, a reagent feeding device for feeding reagents corresponding to an analysis item for each reaction cuvette, to each reaction cuvette on the movable reaction disk, and a photometric device for optically measuring reaction results in solution contained in each reaction cuvette.

Sample pipetting mechanisms 152 and 162 can lift and lower respective provided pipette nozzles to a pipetting position or a discharge position, and rotate the pipette nozzle in a horizontal plane so as to move it between the pipetting and discharge positions.

The sample pipetting mechanism 152 in the first analyzing unit 150 inserts four pipette nozzles into one sample container 10, and pipettes a sample solution in the container 10 into the four pipette nozzles. The sample pipetting mechanism 152 further rotates each of the four nozzles to the discharge position 155 on the reaction disk, and discharges the pipetted sample solution into each of four reaction cuvettes.

The sample pipetting mechanism 162 in the second analyzing unit 160 inserts one pipette nozzle into one sample container 10, and pipettes a sample solution in the container 10 into the pipette nozzle. The mechanism 162 further rotates each of the four nozzles to the discharge position 165 on the reaction disk, and discharges the pipetted sample solution into one reaction cuvette.

The sample pipetting mechanism 152 possesses plural nozzles of which the number or the size is different from that of the sample pipetting mechanism 162, and the different kinds of sample pipetting mechanisms 152 and 162 are provided to correspond to various kinds of pipetting means to be required.

After the pipetting process for the rack 20 has been finished by the analyzing unit 150 or the analyzing unit 160, the rack 20 is transferred by the transfer line 130 and finally collected into the rack collecting unit 170.

In the following, a method of discriminating a type or shape of each sample container, used in the discrimination unit 140, is explained by referring to FIG. 2–FIG. 5.

Figure 2:
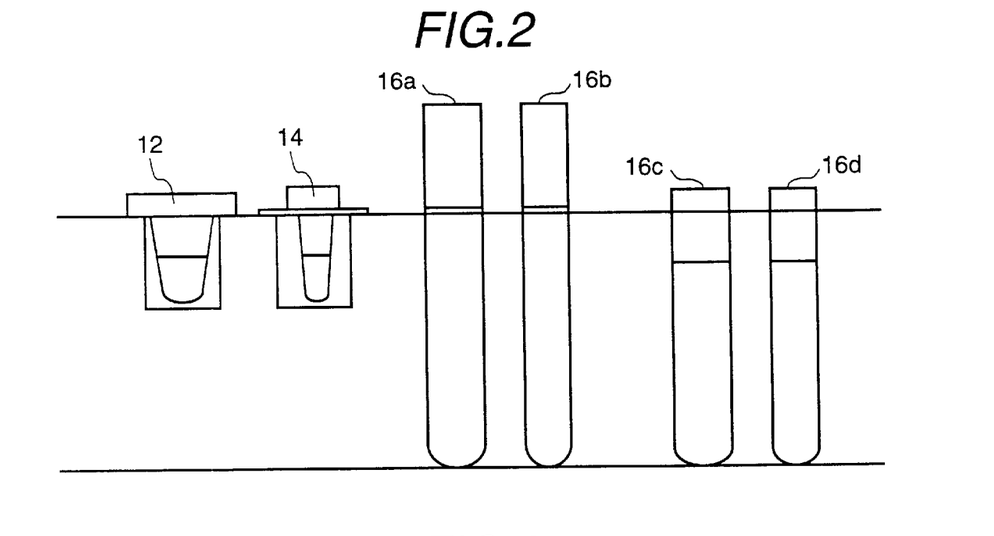
FIG. 2 shows an example of an arrangement state of sample containers used in the analyzing apparatus shown in FIG. 1.

Shapes of sample containers which can be used in the automatic analyzing apparatus 100 shown in FIG. 1 are shown in FIG. 2. Regular containers 12, small quantity measurement containers 14, and test tubes 16a, 16b, 16c and 16d, are used as sample containers in the analyzing apparatus 100. An outer diameter (width) as to each type in the above-mentioned containers 10, and a kind of sample pipetting mechanism applicable to each type of sample container 10, are summarized in Table 1.

As shown in Table 1, a regular container 12 and a small quantity measurement container 14 have the same outer diameter and the same length. However, the diameter of an aperture part and the inner diameter in a small quantity measurement container 14 are smaller than those of a regular container 12, as shown in FIG. 2. Therefore, the amount of a sample which a small quantity measurement container 14 can contain, is smaller.

Furthermore, a test tube 16a and a test tube 16b have the same length, but different outer diameters, respectively, as shown in FIG. 2. A test tube 16c and a test tube 16d have also the same length, but different outer diameters, respectively, as shown in FIG. 2. Moreover, the length of tubes 16a and 16b is longer than the length of test tubes 16c and 16d.

In Table 1, (A/B) and (B) shown as the pipetting mechanisms item indicate kinds of pipetting mechanism applicable to the respective types of sample containers 10. That is, in the embodiment, two kinds of pipetting mechanisms, namely, mechanisms A and B, are prepared, and both of the mechanisms A and B are applicable to a regular container 12 an to test tubes 16a and 16c. On the other hand, the pipetting mechanism B is applicable only to a small quantity measurement container 14, and to test tubes 16b and 16d.

TABLE 1

| Type of sample container | Outer diameter (mm) | Length (mm) | Sample pipetting mechanism | Remarks |
|---|---|---|---|---|
| 12 | 16 | 20 | A / B | Regular |
| 14 | 16 | 20 | B | Small quantity measurement |
| 16a | 16 | 100 | A / B | Test tube |
| 16b | 13 | 100 | B | Test tube |
| 16c | 16 | 75 | A / B | Test tube |
| 16d | 13 | 75 | B | Test tube |

The reason is as follows. The pipetting mechanism B is applicable to a small diameter of an aperture part of a sample container such as a small quantity measurement container 14, a test tube 16b, a test tube 16d and so forth, and the pipetting mechanism A is applicable only to a large diameter of an aperture part of a sample container such as a regular container 14, a test tube 16a, a test tube 16c and so forth. Therefore, both of the pipetting mechanisms A and B are applicable to a regular container 12, a test tube 16a and a test tube 16c. The sample pipetting mechanisms A and B correspond to the sample pipetting mechanism 152 and the sample pipetting mechanism 162 shown in FIG. 1, respectively.

Now, a shape of a sample container cannot be simply specified from only its outer diameter and length, for example, for a container in which a sample generates a precipitate. Therefore, a container in which a sample generates a precipitate is shaped such that its lower part is tapered, and in a container used for a urine sample, the diameter of an aperture part is increased so that the process of pipetting a urine sample from a urine collecting cup can be easily performed. As for containers having the above-mentioned shapes, it is sometimes necessary to detect the diameters at a plurality of heights.

In the following, discriminating types of sample containers held in a rack 20 is explained by referring to FIG. 3. In the rack shown in FIG. 3, for example, a plurality of types of sample containers are held. That is, five test tubes 16*a*, 16*b*, 16*c*, 16*d* and 16*c* are held in the rack 20. A slit (narrow notch) 22 narrower than the width (outer diameter) of each container is formed in both side walls of the rack 20 at the position corresponding to each container so that a part of a held container can be seen through the slit 22.

The test tubes 16*a* and 16*b* are directly held in the rack 20. The tops of the test tubes 16*c* and 16*d* are made all of uniform height by providing container height adjusting adapters 30 at the bottoms of container holding holes to adjust the to heights of the container, as shown in FIG. 3. The test tube 16*c* held at the most right holding position in the rack 20 is directly held in a container holding hole. Adapter discrimination holes 32*a* and 32*b* are formed at each container height adjusting adapter 30. The adapter discrimination holes 32*a* and 32*b*, as is explained later, are used so that a type of an applied adapter can be discriminated by the container type discrimination part 146.

Furthermore, in order to discriminate the rack number of each rack, for example, a bar code label 24 is affixed to predetermined place in the side wall of the rack 20. In the label 24, for example, a four-digit bar code is described.

Moreover, a bar code label 18 to discriminate ID number and other information on each sample container is affixed to the outer surface of each sample container. In the illustrated embodiment, a thirteen-digit code is used as the bar code label 18 in which ID number of a sample, ID code of an executing diagnosis section, a collection date of a sample, etc. are described.

In the following, a composition of the container type discrimination part 146 is explained by referring to FIG. 4.

A detector used in the discrimination part 146 is composed of a light emission part 146A and a light reception part 146B opposite to each other, which sandwich the transfer line 130. The light emission part 146A is composed of light emitting diodes A1, A2 ,A3 , A4 and A5 arranged in an array state at different height positions perpendicular to the transfer line 130. The light reception part 146B is composed of photo-diodes B1, B2 ,B3 , B4 and B5 also arranged in an array state at different height positions perpendicular to the transfer line 130. A1 and B1 are paired and arranged at the same height. Likewise, each pair in the light emitting diodes A2 ,A3 , A4 and A5, and the photo-diodes B2 ,B3 , B4 and B5, are arranged at the same height.

By the pair of A1 and B1, information on a sample container at the height (level) 1 to each holding hole is obtained. Furthermore, by the pairs in the light emitting diodes A2 ,A3 , A4 and AB, and the photo-diodes B2 ,B3 , B4 and B5, information on the sample container at the levels 2, 3, 4 and 5 are respectively obtained.

The container type discrimination part 146 discriminates a type of each sample container held in the rack 20 conveyed on the transfer line 130, based on the information on the sample container at the levels 1, 2, 3, 4 and 5, which is obtained by the pairs in the light emitting diodes A1, A2, A3, A4 and A5, and the photo-diodes B1, B2 ,B3 , B4 and B5.

Figure 4:
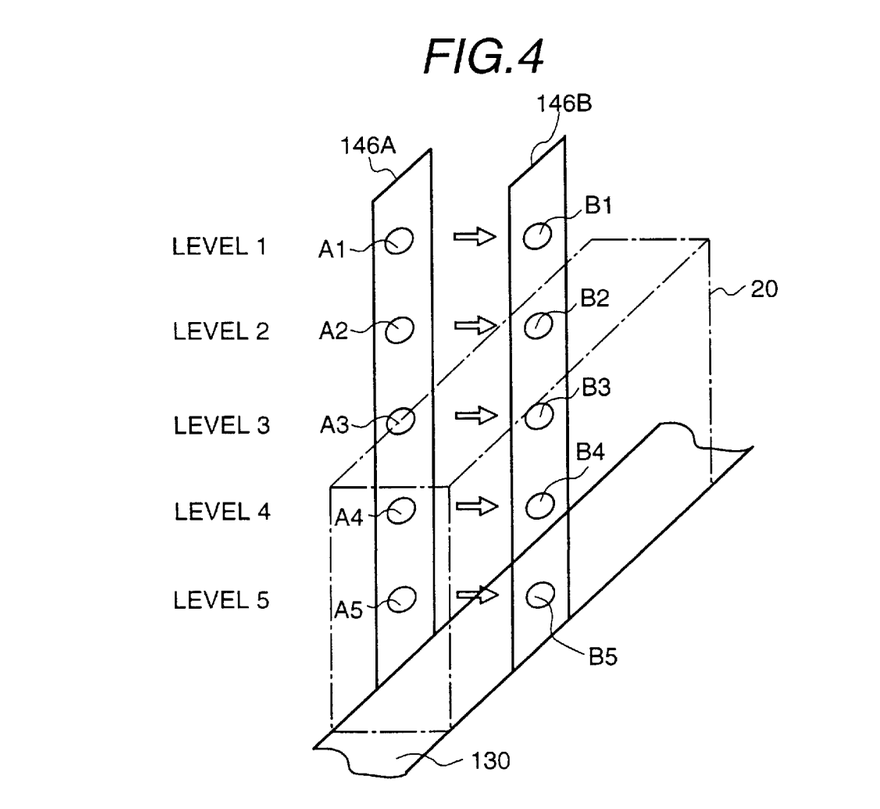
FIG. 4 is an illustration for explaining a detection part of a container type discrimination part in the analyzing apparatus shown in FIG. 1.
Figure 5A:
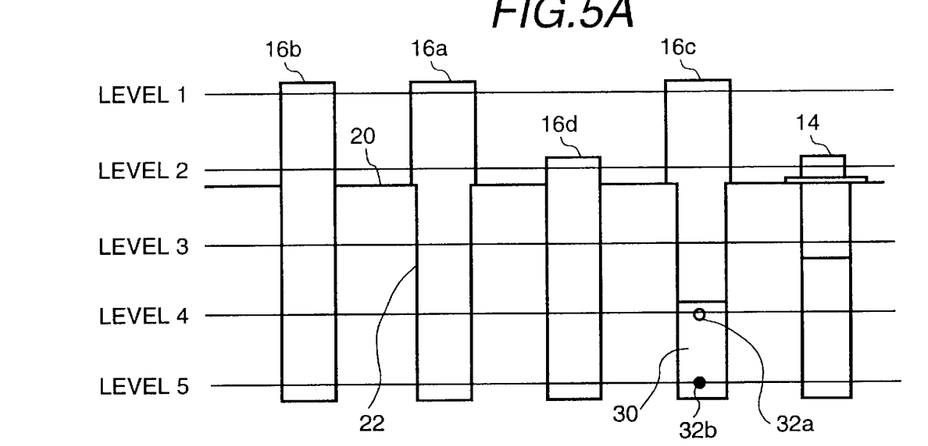
FIG. 5A shows a holding state of various types of sample containers.
Figure 5B:
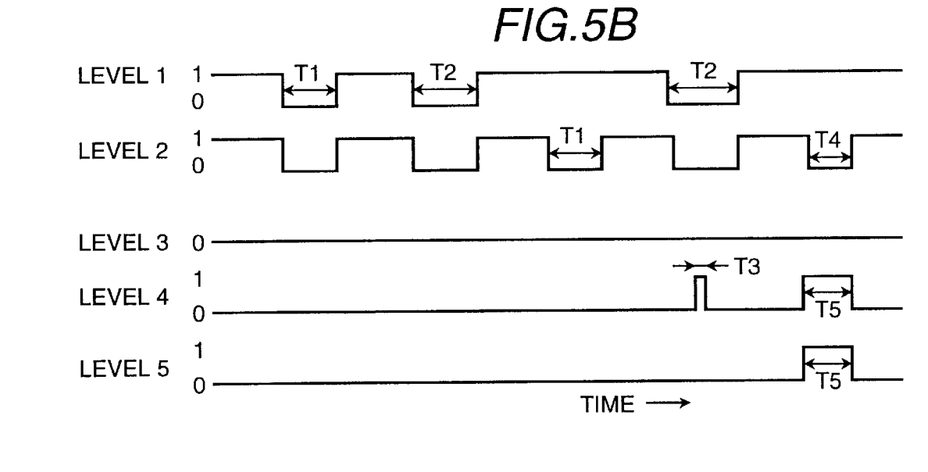
FIG. 5B shows detector signals used for detecting types of the sample containers.

FIG. 5A is a simplified illustration for showing a holding state of a test tube 16*b*, a test tube 16*a*, a test tube 16*d*, a test tube 16*c* held on a container height adjusting adapter 30, and a small quantity measurement container 14, in the rack 20. The relation between the detection levels shown in FIG. 4 and each sample container is also shown in FIG. 5A. Furthermore, FIG. 5B shows output signals which are output from the light reception part of the container discrimination part 146, as to the held sample container shown in FIG. 5A.

The levels 1 and 2 are set so as to detect the presence of a sample container at two levels higher than the top level of the rack 20. The levels 3–5 are set so as to detect the presence or the type of a sample container inside the rack 20, and the container height adjusting adapter 30.

In the following, a method of discriminating a type or shape of each sample container is explained.

At first, discriminating the test tube 16*b* is explained.

As for the test tube 16*b* held in the rack 20, since light emitted from the light emitting diodes A3–A5 is intercepted by the test tube 16*b* at the levels 3–5, the values of output signals from the photo-diodes B3–B5 remain as "0". On the other hand, at the levels 1 and 2, only while the test tube 16*b* exists between the light emitting diodes A1 and A2, and the photo-diodes B1 and B2, the values of output signals from the photo-diodes B1 and B2 indicate "0", otherwise the values of the output signals remain as "1". Since the speed of transferring the rack 20 is constant, the time interval T1 during which light emitted from the light emitting diode A1 is intercepted by the test tube 16*b* moving in the front of the discrimination unit 140 and the value of an output signal from the photo-diode B1 is "0", is proportional to an outer diameter of the test tube 16*b*.

Next, discriminating the test tube 16*a* is explained. As for the test tube 16*a* held in the rack 20, since light emitted from the light emitting diodes A3–A5 is intercepted by the test tube 16*a* at the levels 3–5, the values of output signals from the photo-diodes B3–B5 remain as "0". On the other hand, at the levels 1 and 2, only while the test tube 16*a* exists between the light emitting diodes A1 and A2, and the photo-diodes B1 and B2, the values of output signals from the photo-diodes B1 and B2 indicate "0", otherwise the values of the output signals remain as "1". However, the time interval T2 during which light emitted from the light emitting diode A1 is intercepted by the test tube 16*a* and the value of an output signal from the photo-diode B1 is "0", is longer than the time interval T1. Therefore, although a change pattern of the values of output signals from the photo-diodes B1–B5 for the test tube 16*a* is the same as that for the test tube 16*b*, the test tube 16*a* can be discriminated from the test tube 16*b* by detecting the difference between the time intervals T1 and T2 during which the levels of output signals from the photo-diodes B1 and B2 indicate "0".

Furthermore, discriminating the test tube 16*d* is explained. As for the test tube 16*d* held in the rack 20, at the levels 3–5, since light emitted from the light emitting diodes A3–A5 is intercepted by the test tube 16*d*, the values of output signals from the photo-diodes B3–B5 remain as "0". At the level 1, the value of an output signal from the photo-diode 1 remains as "1". On the other hand, at the level 1, only while the test tube 16*d* exists between the light emitting diode A1 and the photo-diode B1, the value of an output signal from the photo-diode B1 indicates "0", otherwise the value of the output signal remains as "1". The time interval during which light emitted from the light emitting diode A2 is intercepted by the test tube 16*d* and the value of an output signal from the photo-diode B2 is "0", is T1. Although a change pattern of the value of an output signal from the photo-diode B2 for the test tube 16*b* is the same as that for the test tube 16*d*, the test tube 16*b* can be discriminated from the test tube 16c, based on the detected change patterns of output signals from the photo-diode B1 for the two tubes, that is, only the change pattern for the tube 16b at the level 1 indicating "0" level during the time interval T1.

Moreover, discriminating the test tube 16c held on the container height adjusting adapter 30 is explained. As for the test tube 16c held in the rack 20, at the levels 1 and 2, only while the test tube 16c exists between the light emitting diodes A1 and A2, and the photo-diodes B1 and B2, the values of output signals from the photo-diodes B1 and B2 indicate "0", otherwise the values of the output signals remain as "1". At the level 3, since the emitted light is intercepted by the test tube 16c, the value of an output signal from the photo-diode B3 is "0". At the levels 4 and 5, although the emitted light is intercepted by the container height adjusting adapter 30, since the emitted light from the light emitting diode A4 passes through the adapter discrimination hole 32a, the value of an output signal from the photo-diode B4 indicates "1" during the time interval T3. Therefore, the type of the adapter 30 which is used can be determined, based on the detected output signal from the photo-diode 4, and the test tube 16c can be also discriminated, based on the detected time interval T2 of "0" value in output signals from the photo-diodes B1 and B2.

Last, discriminating the small quantity measurement container 14 is explained. As for the small quantity measurement container 14 held in the rack 20, at the level 1, the value of an output signal from the photo-diode B1 remains as "0". On the other hand, at the level 2, the value of an output signal from the photo-diode 1 remains as "1". And, at the level 2, only while the small quantity measurement container 14 exists between the light emitting diode A2 and the photo-diode B2, the value of an output signal from the photo-diode B2 indicates "0", otherwise the level of the output signal remains as "1". At the level 3, since the light emitted from the light emitting diode A3 is intercepted by the small quantity measurement container 14, the value of an output signal from the photo-diode B3 remains as "0". At the levels 4 and 5, since the emitted light is not intercepted by the container 14, the values of output signals from the photo-diodes B4 and B5 indicate "0", while the emitted light passes though the slit 22 corresponding to the container 14, formed at the rack 20. The regular container 12 and the small quantity measurement container 14 are discriminated from other types of sample containers by detecting output signals of "1" level during the time interval T5, from the photo-diodes B4 and B5. The small quantity measurement container 14 can be discriminated from the regular container 12, based on the difference between both time intervals of "0" level in the output signals from the photo-diode B2, for the containers 14 and 12.

As mentioned above, in the embodiment shown in FIG. 4, and FIGS. 5A and 5B, a type of each container can be discriminated by the control part 120, based on the combination of "1/0" patterns in time series of output signals from the photo-diodes B1–B5.

The information on the outer diameters at the predetermined detection levels, as to each sample container, the outer diameters being detected by the container type discrimination part 146, is sent to the control part 120. A memory in the control part 120 stores relations between the information of the outer diameters at the predetermined detection levels, and the time intervals of "1" or "0" level in output signals at the corresponding detection levels from the light reception part 146b, as to each type of a container, as a table in advance.

By examining correspondence between the detected information and the stored information, as to the sample container to be discriminated, the control part 120 can further reconfirm the type of the discriminated sample container.

Furthermore, the control part 120 determines which unit of the first and second analyzing units includes a pipetting mechanism suitable for the discriminated type of each sample container, and transfers the rack 20 holding the sample container to the analyzing unit to be determined as suitable, so that a sample in the sample container is pipetted by the suitable pipetting mechanism, by moving the transfer line 130. For example, as to the test tubes 16a and 16c shown in FIG. 5A, when each of these containers is transferred to the first analyzing unit, the sample in the container is pipetted by the sample pipetting mechanism 152 at the sample pipetting position 154. On the other hand, as to the test tubes 16b and 16d, and the small quantity measurement container 14 shown in FIG. 5A, when each of these containers is transferred to the second analyzing unit, the sample in the container is pipetted by the sample pipetting mechanism 162 at the sample pipetting position 164.

Although discriminating five types of sample containers by using the five light sensors of diodes is explained in the above embodiment, the number of types in sample containers is not restricted to five, and the number of types in sample containers can be changed by changing the number of light sensors, corresponding to the detection resolution in the height direction, which is required to the number of types in sample containers and a way of holding sample containers in the rack 20.

Moreover, in the above embodiment, the outer diameter or width of each sample container is detected by using the relation between the moving speed of the transfer line 130 and the time changes in output signals from the one-dimensional light sensor array. However, the outer diameter or width of each sample container can be also detected without moving the sample container, by providing a two-dimensional light sensor array.

Detection of the presence and discrimination of a type of a container height adjusting adapter 30, can be realized by forming one or more adapter discrimination holes 32 which become light paths in the adapter 30, as shown in FIG. 3.

The control part 120 controls the transfer line 130 to move sample containers held in the rack 20 to the first analyzing unit 150 or the second analyzing unit 160, and controls the pipetting process of a sample in each sample container. In the case of pipetting a sample contained in a sample container, in the first analyzing unit 150, the rack 20 is moved and stopped in the front of the analyzing unit 150, as shown by an arrow mark C, further moved to the position of the pipetting mechanism 152, and the sample in the sample container is pipetted by the sample pipetting mechanism 152. After the sample pipetting is finished, the rack 20 is moved as shown by an arrow mark D, and again conveyed by the transfer line 130. In the case of not pipetting a sample contained in a sample container, in the first analyzing unit 150, the rack 20 passes in the front of the first analyzing unit 150, and it is moved to the position of the second analyzing unit 160. The movement of the rack 20 in the analyzing unit 160 is similar to that in the analyzing unit 150.

The first analyzing unit 150 is, for example, an analyzing unit of a type suitable for analyzing many samples, in which four pipetting nozzles are provided so as to simultaneously pipette four samples. The analyzing unit 150 of the above mentioned type is used to pipette blood serum or urine, and to analyze general analysis items such as blood glucose, GOT, GPT, TP, etc.

The second analyzing unit 160 is, for example, an analyzing unit of a type suitable for analyzing analysis items of low frequency, for example, items analyzed by using an immune nephelometric analysis method.

After the pipetting process of the sample in the containers is finished, the rack 20, in which the sample containers are held, is conveyed by the transfer line 130 to the container collecting part 170, and the analyzing process for the rack 20 is completed.

Although details of a sample analyzing method executed in the analyzing units are not explained, a conventional analyzing method can be applied to the sample analyzing process.

In the following, another method of discriminating a type of a sample container is explained.

In this method, a plurality of exclusive racks corresponding to respective types of sample containers are prepared in advance. For example, a rack in which five test tubes 16*a* of a 16 mm outer diameter are held, a rack in which five test tubes 16*b* of a 13 mm outer diameter are held, a rack with container height adjusting adapters, in which five test tubes 16*c* of a 16 mm outer diameter are held, a rack with container height adjusting adapters, in which five test tubes 16*d* of a 13 mm outer diameter are held, and so forth are prepared. Therefore, an operator has only to hold each of the sample containers to a rack exclusive to a type of the sample container.

Furthermore, in the bar code label 24 affixed to each kind of a rack, the rack number, and information of a type, an outer diameter, the length, etc., of a sample container which can be held in the rack, are described.

If information of an outer diameter or the width of a sample container is described in the bar code label 24 affixed to a rack, the discrimination unit 140 reads the rack number and the information on the outer diameter of sample containers, with a bar code reader 142, and detects the height of each sample container held in the rack, with the container type discrimination part 146 having an optical detector that is shown in FIG. 4. In a memory provided in the control part 120, a reference table stores a relation between each type of a sample container to information of an outer diameter, the length, the presence of a container height adapter, etc., in the type of a sample container. The control part 120 determines the type of a sample container to be discriminated, by comparing the information on an outer diameter of the sample container, which is read on the bar code label 24 by the bar code reader 142, and the information on the length of the sample container, with the information described in the reference table. The operations of each sample container held in the rack 20 are the same as those explained in the previous embodiment.

Moreover, it is also possible to discriminate a type of a sample container from the rack number which is described in the bar code label 24 affixed to the rack. For example, the rack number "0001–1000" is allocated to each rack exclusive to a test tube 16*a* of a 16 mm outer diameter and a 100 mm length, the rack number "1001–2000" is allocated to each rack exclusive to a test tube 16*b* of a 13 mm outer diameter and a 100 mm length, the rack number "2001–3000" is allocated to each rack exclusive to a test tube 16*c* of a 16 mm outer diameter and a 75 mm length, the rack number "3001–4000" is allocated to each rack exclusive to a test tube 16*d* of a 13 mm outer diameter and a 75 mm length, the rack number "4001–5000" is allocated to each rack with a container height adjusting adapter, exclusive to a test tube 16*c* of a 16 mm outer diameter and a 75 mm length, and the rack number "5001–6000" is allocated to each rack with a container height adjusting adapter, exclusive to a test tube 16*d* of a 13 mm outer diameter and a 75 mm length. Thus, a type of a sample container can be also discriminated by reading the rack number on the bar code label 24 affixed to a rack.

In the following, another method of discriminating a type of a sample container is explained.

In this method, by writing information of a type or shape of a sample container in a container bar code label 18 affixed to the sample container in advance, a type of a sample container is discriminated by reading the information of a type or shape on the code label 18. That is, in the case of a 13-digit bar code label 18, the information on a type of a sample container is encoded in two digits of the 13-digit code in the code label 18. For example, the contents "10" of the two digits indicate a test tube 16*a* of a 16 mm outer diameter and a 100 mm length, the contents "20" indicate a test tube 16*b* of a 13 mm outer diameter and a 100 mm length, the contents "30" indicate a test tube 16*c* of a 16 mm outer diameter and a 75 mm length, the contents "40" indicate a test tube 16*d* of a 13 mm outer diameter and a 75 mm length, the contents "50" indicate a regular container 12, and the contents "60" indicate a small quantity measurement container 14. Thus, it is also possible to discriminate a type of a sample container by reading the container bar code with a container bar code reading part 144.

In the following, yet another method of discriminating a type of a sample container is explained.

In this method, a type of a sample container is discriminated by using analysis items of a sample in a sample container. That is, information on a sample is read by the container bar code reading part 144 on the container bar code label 18 affixed to a sample container 18. Sample ID is described in the container bar code label 18. Analysis items related to each sample ID are stored in the memory of the control part 120 in advance. By collating the read sample ID with the stored sample IDs, analysis items for each sample can be specified. For example, the relation between each type of a sample container and analysis items peculiar to blood serum, analysis items peculiar to urine, analysis items peculiar to immune substance, etc., is stored in the memory of the control part 120. Thus, the control part 120 can discriminate a type of a sample container, based on the stored relations between analysis items and each sample ID, and the sample ID read by the container bar code reading part 144.

In the following, yet another method of discriminating a type of a sample container is explained.

In this method, a type or shape of a sample container to be used is allotted to each class of sample in advance, and by reading the class of a sample to be analyzed (which is described in the container bar code label 18 affixed to a sample container) with a bar code reader, a type of the sample container is discriminated. Information on a class of a sample to be analyzed is read on the container bar code label 18 by the container bar code reading part 144. As the information on a class of a sample, sample kinds such as blood serum, blood plasma, urine, cerebrospinal fluid, etc., and sample processing stages such as a pre-process (fraction process of HDL cholesterol, and so forth) are treated. On the other hand, information on a type of a sample container to be used, allotted to each class of sample, is stored in the memory of the control part 120 in advance, and by collating the read class information of a sample to be analyzed, with the stored class information, a type of a container containing the sample can be discriminated.

Furthermore, information of a type of a sample container, for example, a use item of each sample container, such as "container for collecting blood serum", "container for collecting urine", "container for collecting blood glucose", etc., and so forth, is directly printed on each sample container in a readable manner, and by reading the printed information together with the label information on a sample in the sample container by a reading means such as a bar code reading device, the read information on a sample container can be also used to discriminate a type of the sample container. Since each type of a sample container is generally related to analysis items in each analyzing system, each analyzing system can reconfirm the relation between the discriminated type of a sample container and analysis items corresponding to the type, which can prevent a misuse of a sample container to a sample to be analyzed in the analyzing system.

If the information on a type of a sample container cannot be affixed to or printed on the sample container, it is considered a possible way to use a container height adjusting adapter for the sample container for indicating information on a type of the sample container, on a surface of the adapter.

Moreover, if the discriminated type or shape of a sample container is not found in a list of types of sample containers permitted to be held in the present rack, the list being stored in the memory of the control part 120, erroneously performing the pipetting process is prevented, by controlling the pipetting mechanism so as not to execute pipetting operations. When pipetting operations are prohibited by the control part 120, an alarm indicating an occurrence of wrongly holding the sample container in the rack is generated to an operator.

Now, in the pipetting process, by setting the range of operating the pipetting mechanism and the range of searching the liquid surface of a sample, corresponding to each type of a sample container, it is possible to more correctly and certainly control the pipetting process. That is, a pipetting mechanism generally includes a liquid surface detector at the top part of a pipetting nozzle, and starts pipetting operations of a sample after detecting the liquid surface of the sample by using the liquid surface detector. However, if the pipetting operation is started by noise signals, etc., notwithstanding that the top part of the pipetting nozzle does not reach the liquid surface, then the sample is not pipetted, and analysis results indicate "0". Therefore, in such a situation, there is the possibility that some analysis items are erroneously judged as normal. In order to avoid such an error, for example, the range of operating the pipetting mechanism and the range of searching the liquid surface for the test tubes 16a and 16b are set differently from the ranges for the tubes 16c and 16d. Thus, the control part 120 controls so as to operate the pipetting mechanism within the ranges set in advance, corresponding to the discriminated type of a sample container, which can prevent the above mentioned error in the pipetting process.

As mentioned above, in the analyzing apparatus shown in FIG., 1, an operator has only to load sample racks in the rack feeding unit, and thereafter, the discrimination of a type of each sample container, and pipetting and analyzing of each sample, are automatically performed. Therefore, even if it is required that different types of sample containers are transferred in an analyzing apparatus, automatic inspection of samples can be easily realized by adopting the automatic analyzing apparatus of the present invention shown in FIG. 1.

Details of the second feature of the present invention will be explained with an embodiment shown in FIG. 6–FIG. 7.

Figure 6:
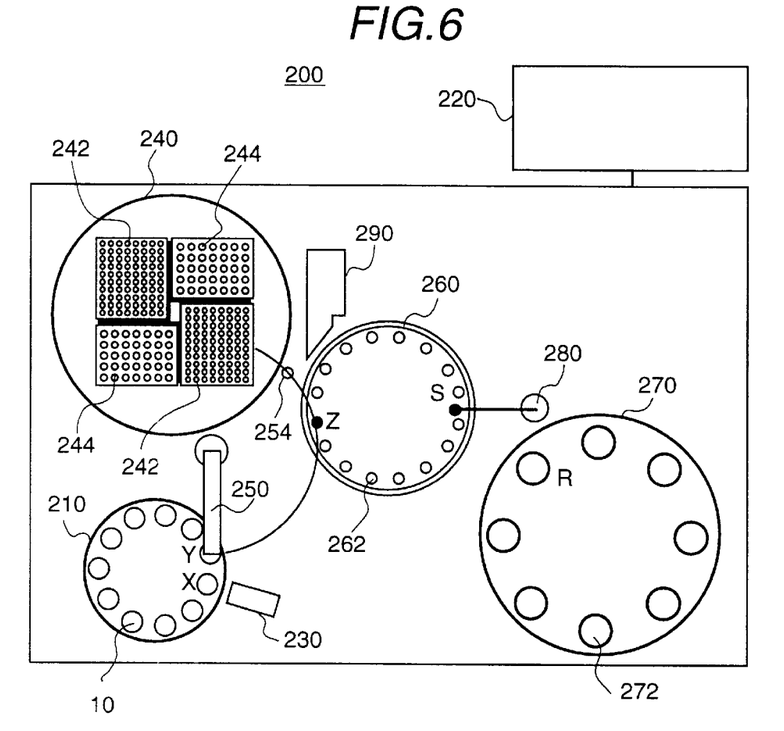
FIG. 6 is a plan view of a composition of an automatic analyzing apparatus in another embodiment of the present invention.

FIG. 6 shows a composition of an analyzing apparatus for liquid samples, in another embodiment of the present invention.

In the analyzing apparatus 200, sample containers 10 are arranged in a turret state on a sample container holder 210. In the figure, eleven sample containers 10 can be held on the sample container holder. At first, a control part 220 rotates the sample container holder 210 to move a sample container to be inspected, to the position X of a sample bar code reading part 230.

The sample bar code reading part 230 reads information described in a sample bar code label affixed to the sample container 10, at the position X. The read information including information on a type or shape of the sample container 10 is sent to the control part 220. In this embodiment, the information on a type or shape of each sample container 10 is written in advance in the information described in the sample bar code label affixed to the sample container 10. The top height of each sample container 10 is held to the predetermined height corresponding to a type of the sample container on the sample container holder 210.

Furthermore, on a turntable 240 as a nozzle chip feeding apparatus, two types of nozzle tips 242 and 244 are prepared, respectively. Respective shapes of the nozzle tips 242 and 244 will be explained by referring to FIG. 7A and FIG. 7B later.

The control part 220 drives a sample pipetting mechanism 250 to a tip connection place for selecting and connecting a nozzle tip of one type selected from the two types of nozzle tips 242 and 244 to a sample pipetting mechanism 250, corresponding to the discriminated type of the sample container 10, based on the read information on a type of the sample container 10. The selected nozzle tip is connected to a connection part provided at the top of a pipette nozzle in the sample pipetting mechanism 250.

Details of the nozzle of the sample pipetting mechanism 250 and the nozzle tips 242 and 244 are explained by referring to FIG. 7A and FIG. 7B later.

Figure 7A:
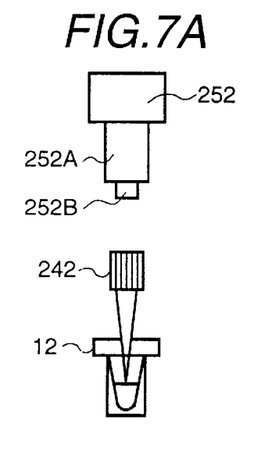
FIG. 7A and FIG. 7B show examples of pipette nozzles in sample pipetting devices used in the analyzing apparatus shown in FIG. 6.
Figure 7B:
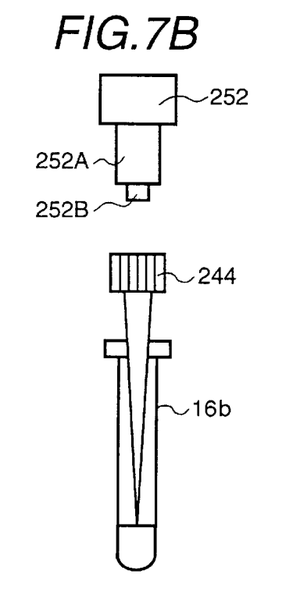

As shown in FIG. 7A and FIG. 7B, a nozzle part 252 possesses a connection part 252A of a large diameter, and connection part 252B of a small diameter, provided at the top of the connection part 252A.

To the connection part 252B, as shown in FIG. 7A, the short nozzle tip 242 of a small diameter is attached. The nozzle tip 242 is used to pipette a sample in a regular containment 12, as shown in the figure.

Furthermore, to the connection part 252A, as shown in FIG. 7B, the long nozzle tip 244 of a large diameter is attached. The nozzle tip 244 is used to pipette a sample in the test tube 16b, as shown in the figure.

Again, the operations of the analyzing apparatus 200 are explained. The sample pipetting mechanism 250 to which a nozzle tip 242 or a nozzle tip 244 is connected, is controlled by the control part 220 to move to a sample pipetting position Y set on the sample container holder 210. Furthermore, the control part 220 moves the sample container in which a sample is to be pipetted, from the position X of the sample bar code reading part 230 to the sample pipetting position Y, by driving the sample container holder 210, and operates the sample pipetting mechanism 250 to pipette the predetermined amount of the sample contained in the sample container 10 into the nozzle tip.

On a reaction table 260, a plurality of reaction containers are arranged in a turret state. In this embodiment shown in FIG. 1, the sample pipetting mechanism 250 is controlled by the control part 220 to move to a sample discharge position Z, and discharge the pipetted sample into a reaction container 262. After pipetting and discharging the sample, the used nozzle tip is discarded each time by disconnecting the nozzle tip from the nozzle 252 and throwing it into a waste hole 254.

Furthermore, on a reagent holding turntable 270, a plurality of reagent containers are arranged in a turret state. In this embodiment shown in FIG. 6, eight reagent containers 272 are arranged on the turntable 270.

The control part 220 drives the reagent holding table 270 based on the analysis items of the sample which were read by the sample bar code reading part 230, so as to move a reagent container 272 corresponding to the read analysis items to a reagent pipetting position R. A reagent pipetter 280 pipettes a reagent in the reagent container 272, and discharges the pipetted reagent into the reaction container 262. The chemical reaction of the sample and the reagent begins thence. The results of the chemical reactions are optically measured by a measurement part 290, and the results for the analysis items to be analyzed for the sample are quantitatively obtained.

As explained above, by applying the analyzing apparatus in this embodiment, it is easily realized that a sample to be analyzed can be pipetted by using a nozzle tip fit for a type of a sample container containing the sample, since it is possible to select a nozzle tip corresponding to a type of a sample container by discriminating a type or shape of a sample container, based on information read by the sample bar code reading part 230, and by selecting one of different sizes of nozzle tips and attaching it to the pipetting nozzle, based on the information on the discriminated type of the sample container.

What is claimed is:

1. An analyzing apparatus transferring at least one sample container in which a sample to be analyzed is contained, pipetting said sample from said sample container to a reaction container, and analyzing said pipetted sample, said analyzing apparatus comprising:

discrimination means for discriminating a type of each sample container containing the sample to be analyzed placed at a discrimination position; and nozzle tip feeding means for allocating and feeding at least one exchangeable pipette nozzle tip, selected for suitability with respect to the discriminated type of sample container from a plurality of different selectable types of exchangeable pipette nozzle tips, to a nozzle part of a pipetting device so as to connect the selected nozzle tip to said nozzle part of said pipetting device;

wherein said pipetting device pipettes said sample contained in said sample container after said selected nozzle tip has been connected to said nozzle part of said pipetting device.

2. An analyzing apparatus according to claim 1, wherein said nozzle tip feeding means can allocate and feed plural types of nozzle tips having different sizes.

3. An analyzing apparatus transferring at of least one sample container in which a sample to be analyzed is contained, pipetting said sample from said sample container to a reaction container, and analyzing said pipetted sample, said analyzing apparatus comprising:

a plurality of types of analyzing units provided for a plurality of types of sampling pipetting devices having at least one of different sizes and numbers of pipette nozzles, each one of said types of analyzing units being prepared corresponding to each one of said types of sampling pipetting devices, and analyzing a sample pipetted by said corresponding one of said types of sampling pipetting devices;

discrimination means for discriminating a type of each sample container placed at a discrimination position; and determining means for determining one of said analyzing units, possessing one of said sample pipetting devices, which is suitable for said discriminated type of said sample container; and transfer means for transferring said discriminated type of sample container to said determined analyzing unit.

4. An analyzing apparatus according to claim 3, wherein said discrimination means discriminates information on the height of the sample container to be discriminated.

5. An analyzing apparatus according to claim 4, further including sample racks, each of which can hold a plurality of sample containers, wherein said discrimination means includes optical detection means for optically detecting information on the height of each sample container held in one of said sample racks.

6. An analyzing apparatus according to claim 5, wherein said discrimination means includes mark reading means for reading information on the width of a sample container, described in marks indicated on a surface of said sample rack in advance, and said determining means determines the suitable analyzing unit for the discriminated type of said sample container based on said information on the width of said sample container and said information on the height of said sample container.

7. An analyzing apparatus according to claim 4, wherein said discrimination means further detects information on the width of said sample container to be discriminated.

8. An analyzing apparatus according to claim 7, wherein said discrimination means includes optical detection means for optically detecting information from said sample container to be discriminated, and wherein the width of said sample container to be discriminated is determined based on a duration time detected by said optical detection means, during which a light beam emitted in said optical detection means is intercepted by said sample container.

9. An analyzing apparatus according to claim 3, wherein said discrimination means includes code mark reading means for reading code marks indicated in advance on a surface of said sample container to be discriminated, said code marks including information on said type of the sample container to be discriminated, and wherein said determining means determines the suitable analyzing unit for the discriminated type of said sample container, based on said information read by said code reading means.

10. An analyzing apparatus according to claim 3, further including memory means for storing types of sample containers permitted to be used in said analyzing apparatus, and control means for controlling said sample pipetting devices so as not to pipette a sample in a sample container if the type of said sample container which is discriminated by said discrimination means does not exist in said types stored in said memory means.

11. An analyzing apparatus transferring at least one sample container in which a sample to be analyzed is contained, pipetting said sample from said sample container to a reaction container, and analyzing said pipetted sample, said analyzing apparatus comprising:

a plurality of types of analyzing units provided for a plurality of types of sampling pipetting devices having at least one of different sizes and numbers of pipette nozzles, each one of said types of analyzing units being prepared corresponding to each one of said types of sampling pipetting devices, and analyzing a sample pipetted by said corresponding one of said types of sampling pipetting devices;

a rack transfer line for transferring a sample rack to hold at least one sample container containing a sample;

discrimination means for discriminating information on an analysis item allocated to said sample container held in said transferred rack;

determining means for determining one of said analyzing units, possessing one of said sample pipetting devices, which possesses a pipette nozzle suitable for said type of sample container to which the analysis item discriminated by said discrimination means has been allocated, based on said discriminated analysis item; and a controller for controlling said rack transfer line so as to convey said sample rack for holding said sample container to which said discriminated item has been allocated, toward said determined analyzing unit;

wherein said sample contained in said sample container to which said discriminated analysis item has been allocated is pipetted by said pipette nozzle that is suitable for said type of sample container to which the discriminated analysis item has been allocated.

* * * * *